(12) United States Patent
McCoy

(10) Patent No.: US 6,840,242 B1
(45) Date of Patent: Jan. 11, 2005

(54) TRACHEOSTOMY ASPIRATION SUCTION TUBE

(76) Inventor: Stephen Craig McCoy, 125 Cottontail Cir., Alvaton, KY (US) 42122

( * ) Notice: Subject to any disclaimer, the term of this patent is extended or adjusted under 35 U.S.C. 154(b) by 0 days.

(21) Appl. No.: 10/349,698

(22) Filed: Jan. 22, 2003

Related U.S. Application Data

(60) Provisional application No. 60/351,027, filed on Jan. 23, 2002.

(51) Int. Cl.[7] ............................................. A61M 16/00
(52) U.S. Cl. .............................. 128/207.14; 128/207.15
(58) Field of Search ...................... 128/207.14, 207.15, 128/207.16, 207.29, 200.26, 205.19; 604/96.01, 103.01–103.03, 6.16, 8–10, 103.07; 623/9, 23.67, 23.7; 606/191, 192, 196, 108

(56) References Cited

U.S. PATENT DOCUMENTS

| | | | | | |
|---|---|---|---|---|---|
| 4,278,081 A | * | 7/1981 | Jones | ..................... | 128/207.15 |
| 4,280,492 A | * | 7/1981 | Latham | ................. | 128/207.15 |
| 4,795,465 A | * | 1/1989 | Marten | ........................... | 623/9 |
| 4,979,505 A | * | 12/1990 | Cox | ...................... | 128/207.15 |
| 5,054,484 A | * | 10/1991 | Hebeler, Jr. | ............ | 128/207.16 |
| 5,056,515 A | * | 10/1991 | Abel | ...................... | 128/207.15 |
| 5,067,497 A | * | 11/1991 | Greear et al. | .......... | 128/207.15 |
| 5,107,828 A | * | 4/1992 | Koss et al. | ............ | 128/200.26 |
| 5,653,231 A | * | 8/1997 | Bell | ...................... | 128/207.16 |
| 6,460,540 B1 | * | 10/2002 | Klepper | ................ | 128/207.14 |
| 6,612,305 B2 | * | 9/2003 | Fauza | .................... | 128/200.26 |
| 2003/0037789 A1 | * | 2/2003 | Klinberg et al. | ....... | 128/207.14 |

* cited by examiner

*Primary Examiner*—Henry Bennett
*Assistant Examiner*—Teena Mitchell
(74) *Attorney, Agent, or Firm*—Laura M. Hagan; Kerrick Stivers & Coyle

(57) ABSTRACT

A tracheostomy aspiration suction tube for management of tracheostomized patients with co-existing dysphagia allowing aspirated material to be collected and removed from the patient prior to traveling toward the lungs. The tracheostomy aspiration suction tube utilizes a primary cannula as a passageway for air to the patient's lungs, while also providing an insertion cannula capable of receiving an inflatable collection receptacle to be placed below the vocal cords. Upon inflation, the collection receptacle forms a seal with the patient's trachea, which effectively catches any aspirated material. Attached to the collection receptacle is a drainage tube connected an external suction device. The aspirated material is suctioned out of the collection receptacle and away from the patient. The collection receptacle can be removed and reinserted as needed.

18 Claims, 7 Drawing Sheets

TRACHEOSTOMY ASPIRATION SUCTION TUBE

This application claims priority to provisional patent application 60/351,027 filed on Jan. 23, 2002.

BACKGROUND OF THE INVENTION

The present invention relates generally to tracheostomy tubes, and more specifically tracheostomy tubes that provide a means to prevent a patient from aspirating secretions, food or fluid while a tracheostomy tube is in use.

The normal structure and function of the aero-digestive tract, including the mouth and pharynx, bounded inferiorly by the larynx, serve to protect the airway by preventing secretions, fluid and/or food from entering the laryngeal space and thereby compromising the airway. When airway protection is ineffective or inefficient, secretions, fluids and/or food may enter the trachea via the true vocal cords and eventually move into the lungs. Any secretion, fluid or food that bypasses normal airway protection and enters beyond the level of the vocal cords is, by definition, aspiration. Various management techniques are available to minimize or prevent aspiration. These include the restriction or cessation of an oral diet and/or the use of compensatory techniques that allow the patient to exert conscious control over the physiological mechanisms of airway protection. For individuals with tracheostomies, aspiration may also be prevented or minimized through the use of artificial airway protection.

Artificial airway protection may be provided through the use of cuffed tracheostomy (trach) tubes or laryngeal stents. Cuffed trach tubes are similar to traditional, cuffless trach tubes, which are basically curved plastic tubes, which provide a passageway for air to the lungs. However, a cuffed trach tube has an inflatable flexible balloon-like cuff attached to the external surface of the distal end of the trach tube. When inflated, the cuff expands to fill the lumen of the trachea. The main purpose of the cuff is to maximize ventilation of the lower airway by preventing the escape of gas (air) via the upper airway. In addition, the inflatable cuff design may temporarily prevent aspirated material from reaching the lungs. However, once the cuff is deflated, aspirated material that remains on top of the cuff is acted upon by gravity and travels downward toward the lung. Thus, the cuffed trach tube does not prevent aspiration, but only delays the aspirated material from reaching the lungs. Moreover, continuous inflation of the cuff may lead to other problems (for example, irritation to the surrounding tissue with prolonged placement of the cuff and/or the colonization of bacteria in the trachea due to inaccessibility of the cuff for cleaning).

Traditional laryngeal stents, another artificial means of aspiration prevention, require a medical procedure to place a physical block within the larynx. Stents are typically used to support tissue grafts and to block off flow through the trachea while the larynx is being reconstructed. Traditional stents are sutured in place, and removal can be quite traumatic. Although stents have proven somewhat effective, they have a very limited application and an unfavorable cost-to-benefit ratio due to the possible complications during placement and subsequent side effects. Moreover, when a traditional laryngeal stent is in place, an individual is not capable of speaking.

Improvements of traditional laryngeal stents have occurred, such as the ones shown in U.S. Pat. No. 5,494,029 issued Feb. 27, 1996 and U.S. Pat. No. 4,794,924 issued Jan. 3, 1989. Both of these stents are inflatable and flexible, with dimensions and configurations which allow the stent to be positioned adjacent to the larynx to contact and support anatomical features in the glottic and supraglottic region of the larynx. The diameter of the stent once inflated is such as to provide a seal above the larynx; thus, it is capable of delaying aspiration. Additionally, the '924 patent includes a unidirectional valve-like arrangement on the rounded upper surface of the stent which allows for venting of pressure from below the larynx, such as when the patient coughs; however, when the patient inhales, the flaps of the valve-like arrangement are drawn together in a closed position. Thus, with both of these devices, once the stent is deflated, any fluid or particulate accumulated on top of the stent is acted upon by gravity and travels downward toward the lungs.

To date, there is no readily available effective method of aspiration management for tracheostomized patients. The tracheostomy aspiration suction tube (TAST) described below provides for an effective means of managing aspiration in tracheostomized patients. The TAST is designed for individuals who require the placement of a tracheostomy tube and who present with difficulty swallowing or dysphagia that results in aspiration. The TAST collects and drains the aspirated material from the trachea, thus preventing it from entering the lower airway where it may lead to respiratory complications. Additionally, the TAST provides a means to remove and clean the collection receptacle and drainage tube used to collect and remove the aspirated material.

SUMMARY OF THE INVENTION

The TAST is similar to a traditional trach tube in that it includes a curved plastic tube or a primary or outer cannula, which provides a patent airway for inhalation and exhalation. Similar to existing cuffed and cuffless tracheostomy tubes, the TAST can be made in various lengths and with various primary cannula dimensions. In addition, it also includes a smaller insertion cannula, through which an inflatable collection receptacle and drainage tube may be inserted. The insertion cannula is either inset within the primary cannula or may run along the upper surface or the wall of the primary cannula. However, the insertion cannula only follows the primary cannula from the one end which is orientated outside the neck of the wearer to just inside the trachea of the wearer, where the insertion cannula ends and opens into the trachea.

The insertion cannula is capable of receiving and provides a passageway for insertion of an inflatable collection receptacle, which is attached to the end of a flexible drainage tube. Initially deflated, the collection receptacle and the attached drainage tube are inserted into the insertion cannula until the collection receptacle is outside the opening at the end of the insertion cannula, within the lumen of the trachea. The collection receptacle is inflated via an inflation line, which is connected to an inflation valve, inset within the lateral wall of the drainage tube and extends the length of the tube until it exits within the sealed collection receptacle. The collection receptacle is inflated until it fills the lumen of the trachea. At the bottom portion of the collection receptacle is a drainage port, which connects to the drainage tube. The collection receptacle, once inflated, will be in the shape of a basket, bowl, funnel or other shape, as long as its shape is such that it channels the flow of aspirated material toward the drainage port. Aspirated material that is collected in the collection receptacle and funneled toward the drainage tube via the drainage port is removed by attaching an external suction device to the external end of the drainage tube.

The design of the TAST allows for several advances in the management of tracheostomized patients with co-existing dysphagia. First, the collection receptacle, when inflated, will be located above the tracheostomy tube and directly below the vocal cords. This allows for material that passes below the vocal cords to be collected by the collection receptacle and guided towards the drainage tube, where it may be removed. Second, the deflated collection receptacle and the drainage tube may be removed via the insertion cannula. Therefore, both the collection receptacle and drainage tube may be cleaned and reinserted as needed. This will reduce the problem of bacterial colonization within the trachea that occurs with use of the traditional cuffed trach tube. The design features of the TAST will also enable patients who have difficulty with aspiration and who have a tracheostomy to continue oral feedings during their dysphagia rehabilitation. Moreover, design features will enable some patients who are chronic aspirators and who have a tracheostomy to continue oral feedings indefinitely. Finally, this device may prove to be a valuable dysphagia assessment and outcome measure tool for tracheostomized patients.

DETAILED DESCRIPTION OF THE DRAWINGS

Figure 1:
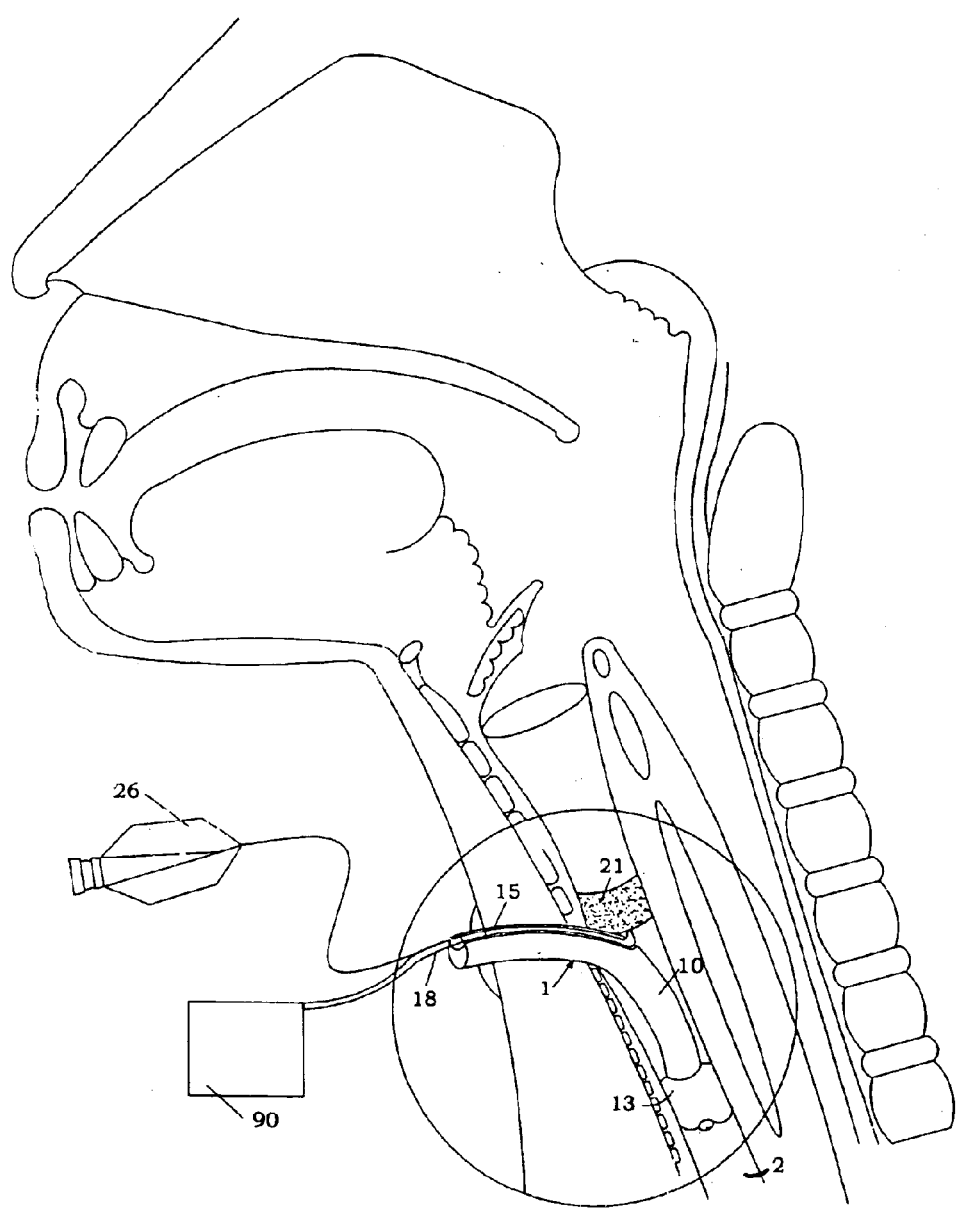
FIG. 1 is a sectional, partially schematic view of a TAST illustrating a preferred embodiment of the present invention installed within the trachea of a patient.
Figure 2:
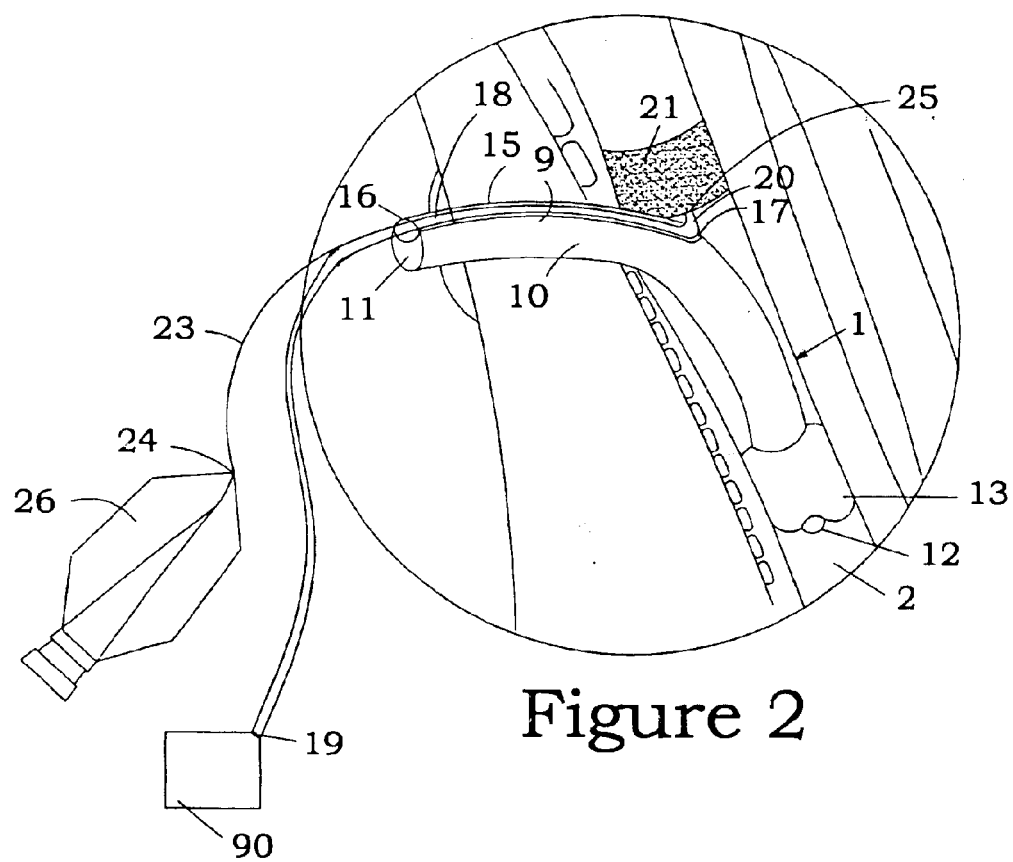
FIG. 2 is a close-up view of the sectional, partially schematic view of a preferred embodiment of the present invention installed within the trachea of a patient.

FIG. 1 and FIG. 2 each disclose a diagram of a TAST 1 inserted in a patient. FIG. 2 is a close-up view of the circled diagram on FIG. 1. The TAST 1 has a primary cannula 10 with a proximal end 11 and a distal end 12, with the proximal end 11 being orientated outside the neck of the wearer and the distal end 12 being orientated within the trachea 2 of the wearer. The primary cannula 10 also has an upper surface or the wall 9 and is curved to fit within the trachea 2 of a patient. FIG. 1 and FIG. 2 show a traditional tracheostomy cuff 13 located at the distal end 12 of the primary cannula 10 which serves to maximize ventilation of the lower airway by preventing the escape of gas via the upper airway. However, the TAST 1 could be constructed without a traditional tracheostomy cuff 13, and instead with a primary cannula 10 similar to that used in a cuffless trach tube. In traditional trach tubes, the primary cannula 10 is tubular or round in shape. While FIGS. 1 and 2 of the TAST 1 show use of a similarly round shaped primary cannula 10, the shape may be varied so that the shape of the primary cannula 10 has a larger circumference, including an ovular or octagonal shape.

Inset within the upper surface or the wall 9 of the primary cannula 10 is an insertion cannula 15, which has an anterior 16 and a posterior end 17. As the primary cannula 10 begins its turn to go further down the trachea 2, the posterior end 17 of the insertion cannula 15 extends through the primary cannula 10. An opening is provided at each of the anterior 16 and posterior ends 17 of the insertion cannula 15.

The insertion cannula 15 provides a passageway for the insertion of an inflatable collection receptacle 21, which is attached to a flexible drainage tube 18. The drainage tube 18 has a first end 19 and a second end 20, with the first end 19 orientated outside of the wearer and the second end 20 connected to a drainage port 22 in the collection receptacle 21. Initially deflated, the collection receptacle 21 and the attached drainage tube 18 are inserted into the insertion cannula 15 until the collection receptacle 21 is outside the opening at the posterior end 17 of the insertion cannula 15, within the lumen of the trachea 2. At this point, the collection receptacle 21 is inflated until it fills the lumen of the trachea 2. The collection receptacle 21 is inflated via an inflation line 23, which has a first 24 and second end 25, with the first end 24 being orientated outside the neck of the wearer and attached to an inflation device 26. The inflation line 23 is inset within the wall of the drainage tube 18 and extends the length of the drainage tube 18 until the second end 25 exits within a self-sealing portal in the collection receptacle 21.

Figure 3:
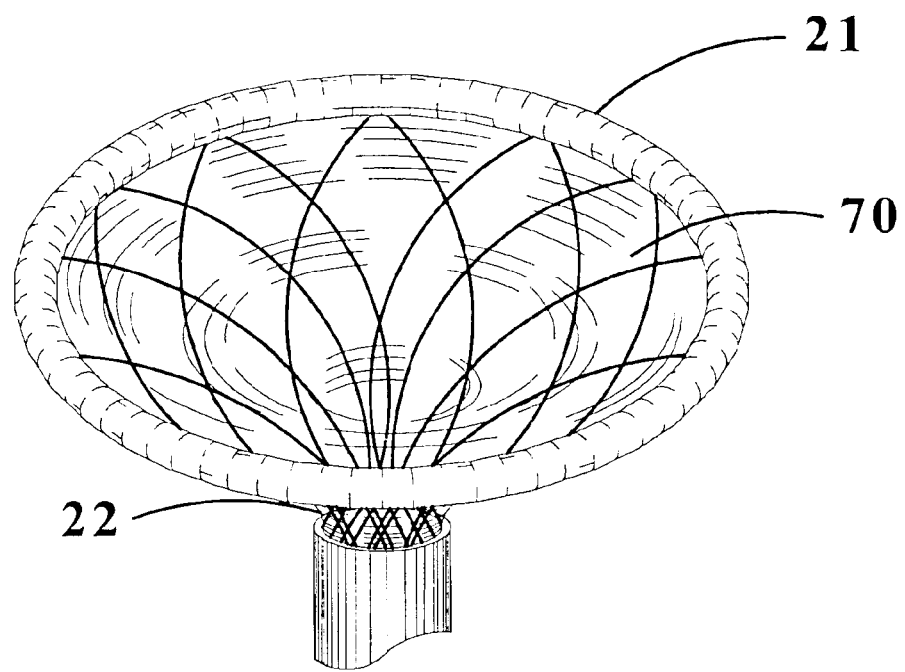
FIG. 3 is a perspective view of a collection receptacle formed with wire and covered in a thin plastic-like film.

The collection receptacle 21 is inflated and/or deflated by an external inflation device 26. An example of an external inflation device 26 is a pump (syringe) connected to the first end 24 of the inflation line 23 capable of injecting air under pressure into or removing air from the collection receptacle 21. Located within the collection receptacle 21 and attached to the second end 25 of the inflation line 23 is a self-sealing portal or a check valve of some time, which is common in the industry. The self-sealing portal or check valve restricts the flow of air once place in the collection receptacle 21 until a release mechanism is activated. The collection receptacle 21, once inflated, can be in the shape of a funnel as is shown in FIG. 3. However, the collection receptacle 21 may also be designed to form other shapes, i.e., a bowl or basket, as long as the shape of the collection receptacle 21 is such that it channels the flow of the aspirated material toward the drainage port 22 located in the bottom of the collection receptacle 21. The drainage port 22 is connected to the second end 20 of the drainage tube 18 and aspirated material that is collected in the collection receptacle 21 and funneled toward the drainage tube 18 is removed by attaching an external suction device 90 to the first end 19 of the drainage tube 18, which is used to pull the aspirated material through the drainage tube 18 and out of the patient. It is also possible that the drainage tube 18 may have a built-in drainage or suction device directly attached to it so no external suction device 90 would be required for removal of the aspirated material.

Removal of the drainage tube 18 and collection receptacle 21 for cleaning or replacement is achieved by deflating the collection receptacle 21 and then pulling on the drainage tube 18, forcing the collapsed collection receptacle 21 through the insertion cannula 15.

While the collection receptacle 21 may be comprised of an entirely inflatable material, it may also be comprised of materials such as nitinol, silastic, stainless steel and/or plastic material of various chemical make-up and density, as is shown in FIG. 3. If the collection receptacle 21 were comprised of one of these materials, then its structure must be one which would allow for the collection receptacle 21 to collapse and conform to the diameter of the insertion cannula 15. Additionally, if the collection receptacle 21 was comprised of one of the above-referenced materials, then it would also be covered in an inflatable thin plastic-like film 70, which would cover the collection receptacle 21. Inflation of the film 70 would provide a soft and deformable cover for the collection receptacle 21, allowing it to substantially conform to the anatomical surface of the trachea 2. The collection receptacle 21 is designed so that the width or diameter of the collection receptacle 21 is such as to provide a seal within the trachea 2.

Figure 4:
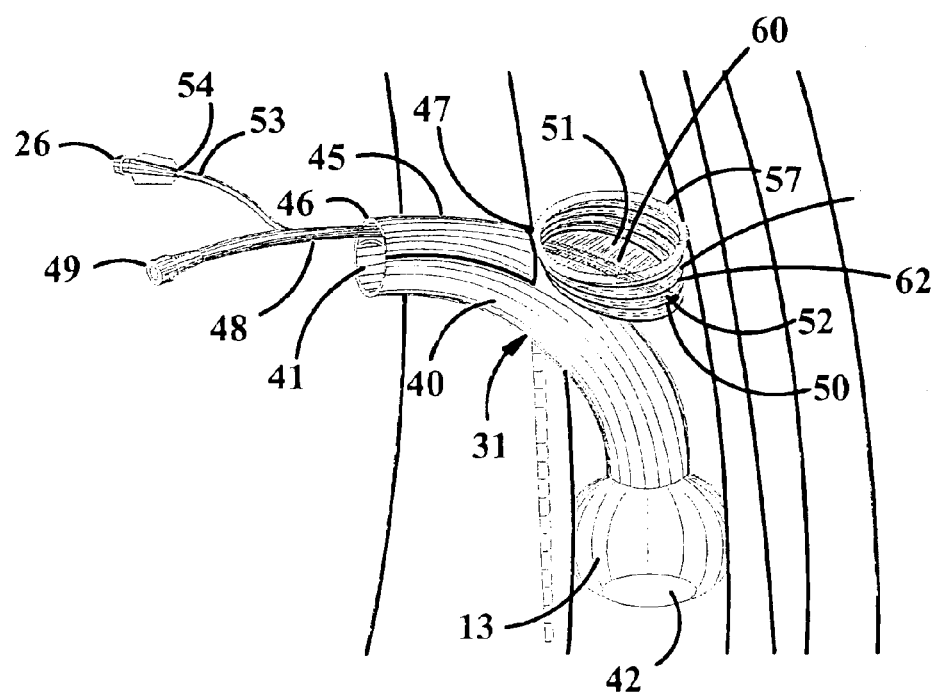
FIG. 4 is a sectional, partially schematic view of TAST illustrating another embodiment of the present invention installed within the trachea of a patient.
Figure 7:
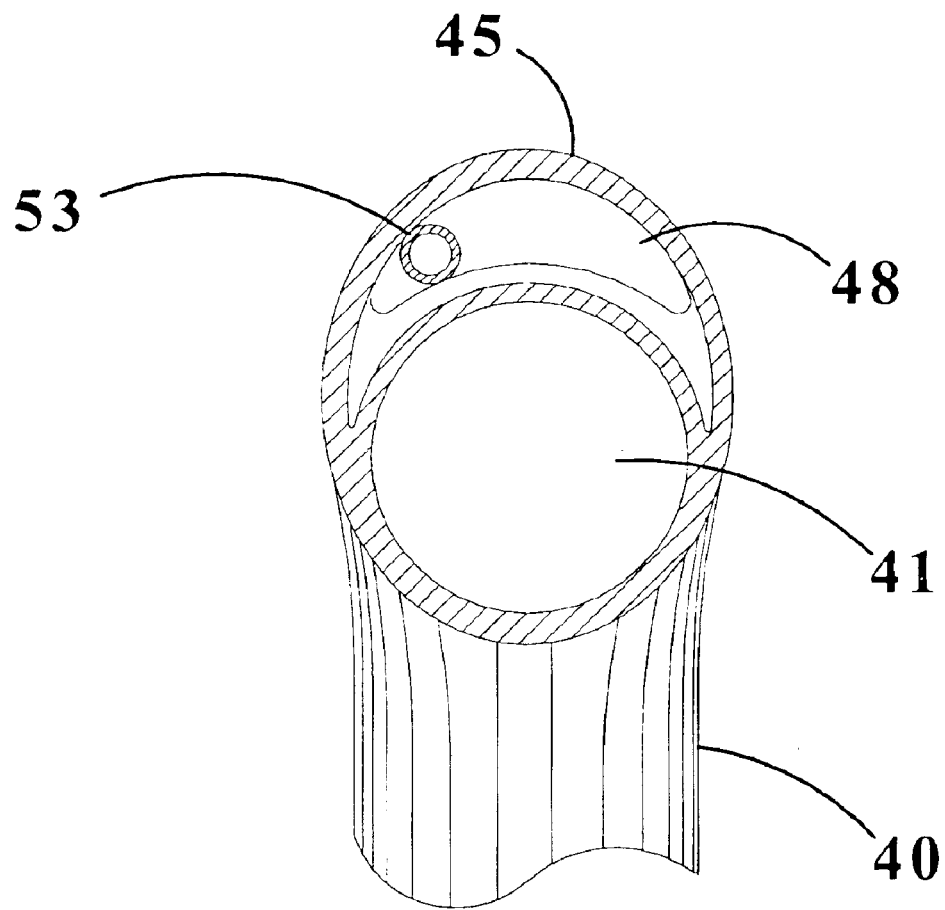
FIG. 7 is a front view of the primary cannula and insertion cannula in an alternative embodiment of the present invention.

An alternative embodiment 31 of the TAST 1 is shown in FIG. 4, which uses a primary cannula 40 similar to the conventional trach tube in that it has an overall curve to meet the requirements of the tracheostomy and a proximal end 41, orientated to fit outside the neck of the wearer and a distal end 42 orientated to fit inside the trachea 2 of the wearer. The primary cannula 40 provides a passageway for air to the lungs as in a conventional trach tube. As is shown in FIG. 7 and FIG. 4, along the upper outer surface 39 of the primary cannula 40, is an insertion cannula 45. FIG. 7 shows how the insertion cannula 45 is crescent in shape and FIG. 4 illustrates how the insertion cannula 45 is approximately the length equal to the straight portion of the primary cannula 40. The insertion cannula 45 has an anterior 46 and posterior end 47, with the anterior end 46 being orientated outside the neck of the wearer and the posterior end 47 being orientated inside the trachea 2 of the wearer. The insertion cannula 45 provides a passageway for insertion of the drainage tube 48 and the collection receptacle 51. In this alternate embodiment 31, a drainage tube 48 with a first 49 and second end 50 is also utilized. The first end 49 of the drainage tube 48 is orientated to be outside the neck of the wearer and attached to an external suction device 90. The second end 50 of the drainage tube 48 is attached to a drainage port 52 located in the bottom surface 60 an inflatable collection receptacle 51.

Figure 5:
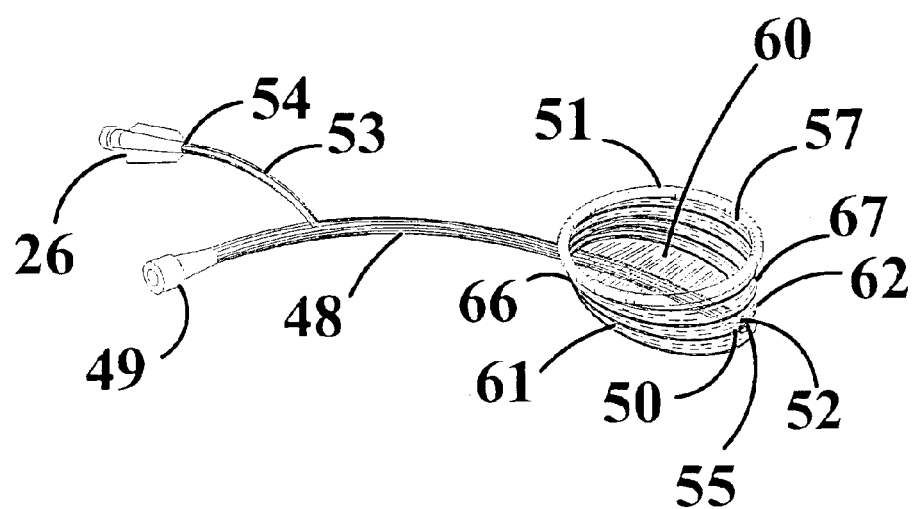
FIG. 5 is a side view a drainage tube, inflation line and collection receptacle of an alternative embodiment of the present invention.
Figure 6:
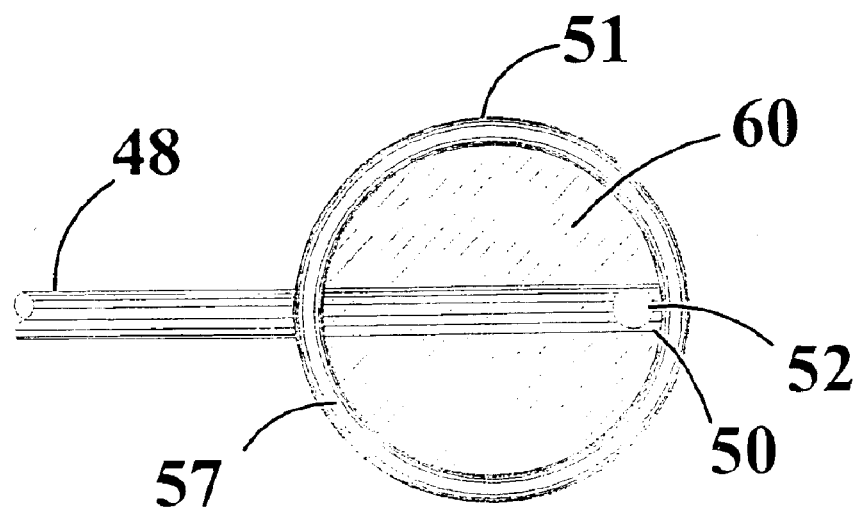
FIG. 6 is a top view of the alternative embodiment of the collection receptacle.

FIGS. 5 and 6 show the collection receptacle 51, which has a flexible bottom 60 and collapsible walls 61 that take the shape of a truncated cylinder. When compressed, it is capable of forming the crescent shape of the insertion cannula 45, as is the case upon insertion or withdrawal of the collection receptacle 51 from the insertion cannula 45. The collection receptacle 51 is approximately circular at the bottom 60 with the circular spiral spring 62 attached to form the walls 61. The fine wire circular spiral spring frame 62 can be made of a super elastic shape memory metal such as Nitinol or spring steel with a small diameter (e.g. 0.009"), approximately that of the trachea 2. The entire collection receptacle 51 is covered by a very flexible, thin plastic-like film 70. The circular spiral spring frame 62 and the thin plastic-like film 70 design allows for maximal flexibility during insertion through the insertion cannula 45 and then total recovery to its expanded shape upon reaching the trachea 2. The first side 66 of the circular spiral spring frame 62 nearest to the attachment of the drainage tube 48 is permanently compressed while the second side 67 of the circular spiral spring frame 62 is free to expand. During insertion, the collection receptacle 51 is completely compressed, forming a circular disc. Once completely inserted and outside of the insertion cannula 45 inside the trachea 2, the collection receptacle 51 expands to take the shape of a truncated cylinder.

Attached to a self-sealing portal, or a check valve, which is commonly used in the medical field, placed within the collection receptacle 51 is an inflation line 53. The inflation line 53 has a first 54 and second end 55 with the first end 54 being orientated to be outside the neck of the wearer and connected to an inflation device 26 and a second end 55 being connected to the self-sealing portal in the collection receptacle 51. The inflation line 53 is inset within the wall of the drainage tube 48. Once the collection receptacle 51 is inserted within the trachea 2 of the wearer, it is inflated to ensure proper sealing between the collection receptacle 51 and the inner trachea wall. The placement of the thin plastic-like film 70 ensures an evenly distributed loading at the rim 57 of the collection receptacle 51 in order to form a seal without excessive force on the tissue. Additionally, the rim 57 of the collection receptacle 51 may be enhanced so as to provide a larger inflatable surface area which would assist in forming a sufficient seal between the collection receptacle 51 and the trachea 2.

A drainage port 52 is located in the bottom surface 60 of the collection receptacle 51. The drainage port 52 connects directly to the second end 50 of the drainage tube 48. The drainage port 52 is used to remove fluid and particulate matter. The position and shape of the collection receptacle 51 will insure that all fluid or particulate matter will move to the drainage port 52 when the patient is in the upright posture. The external suction device 90 is used to pull the collected fluid and particulate matter accumulated in the collection receptacle 51 through the drainage port 52 and drainage tube 48 and out of the patient.

The drainage tube 48 is sufficiently flexible to take the general shape of the crescent channel insertion cannula 45 during insertion, and yet sufficiently rigid to transmit force to the collapsed collection receptacle 51 during insertion in the insertion cannula 45, as well as withstanding negative pressure during material withdrawal. It may be necessary to insert a flexible O-ring stretched around the drainage tube 48 to provide an air seal between the drainage tube 48 and the crescent shaped insertion cannula 45.

Removal of the drainage tube 48 and collection receptacle 51 for cleaning or replacement is achieved by pulling on the drainage tube 48. As the pulling force is applied, the permanently collapsed side first side 66 of the collection receptacle 51 will begin to move through the insertion cannula 45 and, in so doing, cause the uncompressed side part 67 of the collection receptacle 51 to collapse and move through the insertion cannula 45 as the pulling force continues. With both embodiments 1, 31 a cap can be used to seal the end of the drainage tube 18, 48 when not in use for withdrawing fluid or particulate matter.

With either embodiment, once the patient has finished eating and there is no fear of additional aspiration, the collection receptacle 21, 51 can be deflated, via the inflation device 26.

After deflation of the collection receptacle 21, 51, it and the drainage tube 18, 48 is pulled through the posterior end 17, 47 and the length of the insertion cannula 15, 45. Both the drainage tube 18, 48 and the collection receptacle 21, 51 can be completely removed from the insertion cannula 15, 45. Upon removal, the collection receptacle 21, 51 and the drainage tube 18, 48 may be cleansed for reuse. The drainage tube 18, 48 and collection receptacle 21, 51 may then be reinserted as needed by the patient.

Either embodiment of the TAST 1, 31 may also enable it to perform the same purpose as the traditional cuffed trach tube. Once inflated, the collection receptacle 21, 51 may provide the necessary seal to prevent air from escaping through the upper airway during mechanical ventilation, thereby eliminating the need for the traditional cuff 13 near the distal end 12, 42 of the primary cannula 10, 40. Since the collection receptacle 21, 51 is positioned above the stoma, unlike the traditional trach cuff on the traditional trach tube, a pressure-sealing flange to prevent air from escaping through the stoma during mechanical ventilation may be required. The use of the TAST 1, 31 with ventilator-dependent patients would be advantageous, because the collection receptacle 21, 51 could be simply removed if the patient no longer required mechanical ventilation and a cuffless trach tube was preferred to a cuffed trach tube. Likewise, the collection receptacle 21, 51 could easily be reinserted should the need for mechanical ventilation return. Finally, the ability to remove and clean the collection receptacle 21, 51 would reduce the risks for bacterial colonization on the cuff.

I claim:

1. A tracheostomy aspiration suction tube, comprising:
   a primary cannula being defined by a wall, having a proximal end and a distal end;
   an insertion cannula inset within said wall of said primary cannula, said insertion cannula having an anterior end and a posterior end;
   said posterior end of said insertion cannula extending through said wall of said primary cannula;
   an inflatable collection receptacle having a drainage port;
   a drainage tube being defined by a wall and having a first end and a second end, said second end attached to said drainage port of said collection receptacle, and said drainage tube extending through said insertion cannula;
   an inflation line inset within said wall of said drainage tube, with a first end and a second end, said second end attached to said inflatable collection receptacle.

2. The tracheostomy aspiration suction tube of claim 1 wherein said collection receptacle when is the shape of a funnel.

3. The tracheostomy aspiration suction tube of claim 1 wherein said inflated collection receptacle is the shape of a bowl.

4. The tracheostomy aspiration suction tube of claim 1 wherein said inflated collection receptacle is the shape of a basket.

5. The tracheostomy aspiration suction tube of claim 1 wherein said drainage tube and said collection receptacle are sized so as to fit within said insertion cannula.

6. The tracheostomy aspiration suction tube of claim 1 wherein said first end of said drainage tube is connected to an external suction device.

7. The tracheostomy aspiration suction tube of claim 1 wherein said first end of said inflation tube is connected to an inflation device.

8. A tracheostomy aspiration suction tube comprising;
   a primary cannula being defined by a wall, having a proximal end and a distal end;
   an insertion cannula attached to said wall of said primary cannula;
   said insertion cannula having an anterior end and a posterior end;
   an inflatable collection receptacle having a drainage port;
   a drainage tube being defined by a wall and having a first end and a second end, said second end attached to said drainage port of said collection receptacle, and said drainage tube extending through said insertion cannula;
   an inflation line set within said wall of said drainage tube, with a first end and a second end, said second end attached to said collection receptacle.

9. The tracheostomy aspiration suction tube of claim 8 wherein said collection receptacle has a flexible bottom and collapsible walls.

10. The tracheostomy aspiration suction tube of claim 8 wherein said bottom of said collection receptacle is circular and said walls are comprised of a circular spiral spring.

11. The tracheostomy aspiration suction tube of claim 10 wherein said circular spiral spring has a first and second side and said first side is compressed and said second side is capable of expanding.

12. The tracheostomy aspiration suction tube of claim 8 wherein said collection receptacle is covered by a thin plastic-like film.

13. The tracheostomy aspiration suction tube of claim 8 wherein the insertion cannula is crescent shaped.

14. The tracheostomy aspiration suction tube of claim 1 wherein said collection receptacle is collapsible.

15. The tracheostomy aspiration suction tube of claim 8 wherein said anterior end of said insertion cannula is located at said proximal end of said primary cannula and said posterior end of said insertion cannula extends to the portion of said primary cannula which enters the trachea of the wearer.

16. The tracheostomy aspiration suction tube of claim 8 wherein said drainage tube and said collection receptacle are sized so as to fit within said insertion cannula.

17. The tracheostomy aspiration suction tube of claim 8 wherein said first end of said drainage tube is connected to an external suction device.

18. The tracheostomy aspiration suction tube of claim 8 wherein said first end of said inflation tube is connected to an inflation device.

* * * * *

UNITED STATES PATENT AND TRADEMARK OFFICE
CERTIFICATE OF CORRECTION

PATENT NO. : 6,840,242 B1
APPLICATION NO. : 10/349698
DATED : January 11, 2005
INVENTOR(S) : McCoy et al.

It is certified that error appears in the above-identified patent and that said Letters Patent is hereby corrected as shown below:

On title page Item (76) please add:
Charles F. Knapp
110 Sheldrake Ct.
Georgetown, KY (US) 40324

Signed and Sealed this

Fifteenth Day of August, 2006

JON W. DUDAS
*Director of the United States Patent and Trademark Office*